US006613767B1

(12) United States Patent
Nijkerk et al.

(10) Patent No.: US 6,613,767 B1
(45) Date of Patent: *Sep. 2, 2003

(54) STABLE AQUEOUS FOLINATE SOLUTION

(75) Inventors: Alfred James Nijkerk, Amsterdam (NL); Johanna M. P. Vermeer, Lisse (NL)

(73) Assignee: Pharmachemie B.V., Haarlem (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 1258 days.

(21) Appl. No.: 08/726,803

(22) Filed: Oct. 7, 1996

Related U.S. Application Data

(63) Continuation-in-part of application No. PCT/NL95/00126, filed on Apr. 4, 1995.

(30) Foreign Application Priority Data

Apr. 5, 1994 (NL) ............................................. 9400530

(51) Int. Cl.⁷ ........................................... A61K 31/495
(52) U.S. Cl. ....................................................... 514/249
(58) Field of Search ......................................... 514/249

(56) References Cited

U.S. PATENT DOCUMENTS

| 2,695,860 A | 11/1954 | Weidenheimer et al. ...... 167/65 |
| 5,134,235 A | 7/1992 | Mueller et al. |
| 5,173,488 A * | 12/1992 | Haeger ........................ 514/249 |
| 5,347,005 A | 9/1994 | Mueller et al. |

FOREIGN PATENT DOCUMENTS

| EP | 0 293 029 | 11/1988 |
| EP | 0293029 A1 | 11/1988 |
| EP | 0 401 895 | 12/1990 |
| EP | 0 667 159 | 8/1995 |
| EP | 0667159 A2 | 8/1995 |
| WO | WO 90/10460 | 9/1990 |
| WO | 90/10460 | 9/1990 |
| WO | 95/26963 | 10/1995 |

OTHER PUBLICATIONS

*Hagers Handbuch der Pharmazeutischen Praxis* (1971), p. 39—"Stabilizers".
Remington's Pharmaceutical Sciences (15$^{th}$ Ed.) Hoover et al., Mack Pub. Co, Easton, PA. (1975) pp. 268–270 and 283–284.*
Massachusetts General Hospital, Dept. of Pharmacy, Dept. of Nursing, Critical Care, "Tromethamine, Tris Buffer" http://www.mgh.haruard.edu/pharmacy/ICU%2 guidelines/tromethamine.htm, Mar. 7, 2003.*
Hagers Handbook of the Pharmaceutical Practice, 1971, p. 358, (Germany).

* cited by examiner

*Primary Examiner*—Theodore J. Criares
(74) *Attorney, Agent, or Firm*—Browdy and Neimark, P.L.L.C.

(57) ABSTRACT

A stable aqueous solution of folinic acid of up to about 400 mg/ml, which does not crystallize at refrigeration temperatures, is obtained by preparing an aqueous solution of sodium folinate.

14 Claims, No Drawings

STABLE AQUEOUS FOLINATE SOLUTION

This application is a continuation-in-part of PCT application PCT/NL95/00126, filed Apr. 4, 1995, the entire contents of which is hereby incorporated herein by reference.

The invention relates to a stable aqueous folinate solution.

Folinic acid is a metabolite of folic acid and is the active form into which folic acid is converted in the body. This conversion is inhibited by some cytostatics such as methotrexate. In order to overcome this problem, folinic acid has to be added. Folinic acid is further used in the case of folic acid deficiency, and it has a synergistic effect in combination with 5-fluorouracil. The customary form in which folinic acid is added is calcium folinate which is administered by infusion or injection. Calcium folinate is readily soluble but it does not keep at room temperature and therefore cannot be stored for prolonged periods at room temperature. At refrigerator temperatures, where the folinate does store well, a relatively concentrated solution is not stable; at the normal refrigerator temperature of approximately 4° C., crystallization takes place at a concentration of as little as 15 mg/ml.

EP 0 401 895 provides folinate solutions with a relatively high concentration which are stable at refrigerator temperature. These solutions contain folinate ions, calcium ions and a complexing agent for calcium. The complexing agent and calcium form a complex. These solutions may be stable at refrigerator temperature in a concentration of as much as 50 mg/ml of folinate. The complexing agent used can be, for example, a sodium salt of ethylenediaminetetraacetic acid.

It has been found that a stable aqueous solution of folinic acid can be obtained simply by preparing an aqueous solution of sodium folinate. Even in a high concentration, up to about 400 mg of folinic acid per ml, it is stable in the refrigerator, i.e., does not crystallize. The aqueous solution of sodium folinate has a concentration of folinic acid in the range of about 15 to 400 mg/ml, preferably in the range of about 15 to 40 mg/ml or in the range of about 20 to 400 mg/ml, and more preferably in the range of about 25 to 400 mg/ml. The solution is stable at a pH range of 4.0 to 10.0, especially from 6.0 to 10.0, and preferably about 8.0 to 9.0.

Preferably, the solution contains a stabilizer, such as sodium citrate or sodium acetate. These salts further increase the stability of the solution. The present folinate solution also comprises an isotonizing agent such as sodium chloride.

It is also advantageous to incorporate a pharmaceutically acceptable buffer into the aqueous folinate solution according to the invention. Such a pharmaceutically acceptable buffer is preferably tris, a phosphate or a carbonate buffer, and is present in a concentration which is effective for obtaining the required pH.

The invention is further explained in the following examples.

EXAMPLE 1

The following injection fluid was prepared:

| | |
|---|---|
| Folinic acid (as sodium folinate) | 25 mg |
| Sodium chloride | 4.3 mg |
| Sodium citrate | 0.5 mg |
| Water for injection to make up to | 1 ml |

The pH had been set to a value of 7.5 by means of sodium hydroxide. The purpose of the sodium chloride was to make the solution isotonic.

The above mentioned solution was found to be still stable after 3 months at refrigerator temperature between 2 and 8° C. (on average approximately 4° C.), i.e., it had not crystallized out.

EXAMPLE 2

The following injection fluid was prepared:

| | |
|---|---|
| Folinic acid (as its sodium salt) | 25.0 mg |
| Sodium citrate | 0.50 mg |
| Sodium chloride | 4.00 mg |
| Tris | 1.21 mg |
| Sodium hydroxide/hydrogen chloride | q.s. (pH 8.0) |
| Water for injection to make up to | 1 ml |

The thus obtained injection fluid was still stable after 3 months at refrigerator temperature.

EXAMPLE 3

An injection fluid was prepared, having the following components:

| | |
|---|---|
| Folinic acid (as its sodium salt) | 25.0 mg |
| Sodium citrate | 0.25 mg |
| Sodium chloride | 4.00 mg |
| Tris | 1.21 mg |
| Sodium hydroxide/hydrogen chloride | q.s. (pH 9.0) |
| Water for injection to make up to | 1 ml |

The obtained injection fluid was still stable after 3 months at refrigerator temperature.

EXAMPLE 4

An injection fluid was prepared, having the following components:

| | |
|---|---|
| Folinic acid (as its sodium salt) | 25.0 mg |
| Sodium citrate | 0.50 mg |
| Sodium chloride | 4.00 mg |
| Sodium hydroxide/hydrogen chloride | q.s. (pH 7.5) |
| Water for injection to make up to | 1 ml |

This injection preparation was still stable after 3 months at refrigerator temperature.

EXAMPLE 5

An injection fluid was prepared, having the following components:

| | |
|---|---|
| Folinic acid (as its sodium salt) | 25.0 mg |
| Sodium citrate | 0.25 mg |
| Sodium acetate | 0.25 mg |
| Sodium chloride | 4.00 mg |
| $NaH_2PO_4.1H_2O$ | 0.134 mg |
| $Na_2HPO_4.2H_2O$ | 1.61 mg |
| Sodium hydroxide/hydrogen chloride | q.s. (pH 8.0) |
| Water for injection to make up to | 1 ml |

This preparation was still stable after 3 months at refrigerator temperature.

EXAMPLE 6

An injection fluid was prepared, having the following components:

| | |
|---|---|
| Folinic acid (as its sodium salt) | 25.0 mg |
| Glucose | 25.0 mg |
| Sodium citrate | 0.50 mg |
| Tris | 1.21 mg |
| Sodium hydroxide/hydrogen chloride | q.s. (pH 8.0) |
| Water for injection to make up to | 1 ml |

This injection preparation was still stable after 3 months at refrigerator temperature.

EXAMPLE 7

I. Shelf Life Tests

Tests were carried out with sodium folinate bulk solutions of 200 ml containing 25, 100, 250 and 400 mg sodium folinate/ml respectively as indicated in Table 1. Each bulk solution was prepared with a 2% excess of sodium folinate, because during autoclaving ca. 2% folinic acid decomposes. Subsequently, 2.15 ml of each formulated solution was used to fill 2R bottles to the exclusion of air. Afterwards, the bottles were then autoclaved at 121° C. for 7 min. The bottles were thereafter stored at 40° C./75% RH (RH= relative humidity). The following analyses were carried out initially at the beginning of the test and after two weeks:

- appearance
- pH
- oxygen percentage in the headspace
- content of folinic acid and decomposition products.

The results are summarized in the Tables 2–5 for the accelerated shelf life tests of the sodium folinate injection preparation having a content of sodium folinate of 25 mg/ml, 100 mg/ml, 250 mg/ml and 400 mg/ml, respectively. The bottles were stored at 40° C./750 RH during the two week time period for the shelf life tests.

TABLE 2

Sodium Folinate Injection, 25 mg/ml

| | Time period | |
|---|---|---|
| Parameters | Initially | 2 weeks |
| Appearance | Clear, yellow solution | Clear, yellow solution |
| pH | 7.5 | 7.0 |
| Percentage oxygen in headspace: mean range | 3.9% (n = 5) 1.8–5.6% | 1.1% (n = 4) 0.1–2.8% |
| Assay folinic acid | 99.7% | 96.3% |
| Assay N-(4-amino-benzoyl glutaminic acid | 0.3% | 0.8% |
| Assay N-10-formyl-folic acid | <0.1% | 0.3% |
| Assay folic acid | n.d.* | n.d.* |
| Total amount of additional peaks | 1.1% | 2.5% |
| Main individual unknown peak | 0.4% | 0.8% |

*n.d. means "not detected"

TABLE 3

Sodium Folinate Injection, 100 mg/ml

| | Time period | |
|---|---|---|
| Parameters | Initially | 2 weeks |
| Appearance | Clear, yellow solution | Clear, yellow solution |
| pH | 7.1 | 7.1 |
| Percentage oxygen in headspace: mean range | 4.3% (n = 5) 3.3–5.3% | n.d. (n = 4) |
| Assay folinic acid | 101.3% | 98.9% |
| Assay N-(4-amino-benzoyl glutaminic acid | 0.4% | 0.9% |
| Assay N-10-formyl-folic acid | 0.1% | 0.3% |
| Assay folic acid | n.d.* | <0.1% |
| Total amount of additional peaks | 1.3% | 2.4% |
| Main individual unknown peak | 0.6% | 1.0% |

*n.d. means "not detected"

TABLE 1

Compositions of Formulations of Sodium Folinate Injections (2R bottle).

| | Concentration of Folinic Acid | | | |
|---|---|---|---|---|
| Product | 25 mg/ml | 100 mg/ml | 250 mg/ml | 400 mg/ml |
| Sodium folinate | 5.57 g (102%) | 22.3 g (102%) | 55.7 g (102%) | 89.2 g (102%) |
| Sodium citrate | 100 mg | 100 mg | 100 mg | 100 mg |
| Sodium chloride | 1000 mg | 1000 mg | 1000 mg | 1000 mg |
| 1N NaOH/1N HCL | up to pH 7.8 ± 0.2 | up to pH 7.8 ± 0.2 | up to pH 7.8 ± 0.2 | up to pH 7.8 ± 0.2 |
| Water for injection | up to 200.0 ml | up to 200.0 ml | up to 200.0 ml | up to 200.0 ml |

The amount of sodium folinate must yet be corrected for the content of sodium folinate in the raw material.

TABLE 4

Sodium Folinate Injection, 250 mg/ml

| | Time period | |
|---|---|---|
| Parameters | Initially | 2 weeks |
| Appearance | Clear, yellow-brown solution | Clear, yellow-brown solution |
| pH | 7.3 | 7.2 |
| Percentage oxygen in head- | 2.6% (n = 5) | n.d. (n = 4) |

TABLE 4-continued

Sodium Folinate Injection, 250 mg/ml

| Parameters | Time period | |
|---|---|---|
| | Initially | 2 weeks |
| space: mean range | 1.2–2.5% | |
| Assay folinic acid | 101.3% | 100.9% |
| Assay N-(4-amino-benzoyl glutaminic acid | 0.4% | 0.9% |
| Assay N-10-formyl-folic acid | 0.1% | 0.1% |
| Assay folic acid | n.d.* | n.d.* |
| Total amount of additional peaks | 1.3% | 1.9% |
| Main individual unknown peak | 0.6% | 0.6% |

*n.d. means "not detected"

TABLE 5

Sodium Folinate Injection, 400 mg/ml

| Parameters | Time period | |
|---|---|---|
| | Initially | 2 weeks |
| Appearance | Clear, yellow-brown solution | Clear, yellow-brown solution |
| pH | 7.5 | 7.3 |
| Percentage oxygen in headspace: mean range | 2.0% (n = 5) 0.8–2.8% | n.d. (n = 4) |
| Assay folinic acid | 91.9%* | 91.6% |
| Assay N-(4-amino-benzoyl glutaminic acid | 0.5% | 0.8% |
| Assay N-10-formyl-folic acid | <0.1% | <0.1% |
| Assay folic acid | n.d.** | n.d. |
| Total amount of additional peaks | 1.5% | 1.8% |
| Main Individual unknown peak | 0.7% | 0.6% |

*The content of folinic acid is lower than the expected theoretical amount of 100%. Filtration of this solution took more time then with the other 3 bulk solutions.
**n.d. means "not detected"

The pH of all four formulations has been set before autoclaving to 7.8±0.2. After autoclaving the pH of the sodium folinate injections of 25, 100, 250 and 400 mg/ml, respectively, decreased to 7.5, 7.1, 7.3 and 7.5, respectively. This pH reduction is probably due to the formation of the decomposition product N-(4-amino benzoyl glutaminic acid) in an amount of 0.3–0.5%.

It appears from the results that the percentage of oxygen in the headspace of the sodium folinate injection preparation decreases to 1% (25 mg/ml formulation) or is no longer detectable (the other three remaining formulations) after storage for two weeks at 40° C./75% RH.

Surprisingly, the higher the content of sodium folinate in the formulation, the smaller the decrease in the content after two weeks at 40° C./75% RH. In all four formulations there was an increase of 0.3–0.5% in the generation of the decomposition product N-(4-amino benzoyl glutaminic acid). This is probably the cause of the decrease in pH after two weeks storage at 40° C./75% RH. On the basis of the present results it is concluded that the sodium folinate injection preparations stabilize with higher concentration of sodium folinate in the preparation.

II. Crystallization Tests

The injection preparations shown in Table 1 were prepared and stored at 4° C. to examine whether these preparations remained stable or not, i.e., whether or not crystallization took place. After storage for one month at 4° C., crystallization was not observed in any of the four preparations of Table 1.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

What is claimed:

1. An aqueous folinate solution for pharmaceutical applications consisting essentially of
   (i) sodium folinate, said sodium folinate being present in an effective amount at a concentration of up to 400 mg folinic acid per ml,
   (ii) a stabilizer selected from the group consisting of sodium citrate, sodium acetate, and mixtures thereof,
   (iii) optionally, an isotonizing agent, and
   (iv) optionally, a buffer selected from the group consisting of tris, phosphate and carbonate buffers.

2. The aqueous folinate solution according to claim 1, wherein the pH of the solution is from about 8.0 to about 9.0.

3. The aqueous folinate solution according to claim 1, wherein said solution contains said isotonizing agent.

4. The aqueous folinate solution according to claim 5, wherein said isotonizing agent is sodium chloride.

5. The aqueous folinate solution according to claim 1, wherein said solution contains said buffer.

6. The aqueous folinate solution according to claim 1, wherein said concentration of sodium folinate is in the range of about 15 to 40 mg of folinic acid per ml.

7. The aqueous folinate solution according to claim 1, wherein said concentration of sodium folinate is in the range of about 20 to 400 mg of folinic acid per ml.

8. The aqueous folinate solution according to claim 1, wherein said concentration of sodium folinate is in the range of about 100 to 400 mg of folinic acid per ml.

9. The aqueous folinate solution according to claim 2, wherein said concentration of sodium folinate is in the range of about 100 to 400 mg of folinic acid per ml.

10. The aqueous folinate solution according to claim 3, wherein said concentration of sodium folinate is in the range of about 100 to 400 mg of folinic acid per ml.

11. The aqueous folinate solution according to claim 4, wherein said concentration of sodium folinate is in the range of about 100 to 400 mg of folinic acid per ml.

12. The aqueous folinate solution according to claim 5, wherein said concentration of sodium folinate is in the range of about 100 to 400 mg of folinic acid per ml.

13. An aqueous folinate solution of sodium salts for pharmaceutical applications, consisting of
   sodium folinate in a concentration of about 15 to 400 mg folinic acid per ml,
   a stabilizer selected from the group consisting of sodium citrate, sodium acetate, and mixtures thereof,
   optionally, an isotonizing agent,
   optionally, a buffer selected from the group consisting of tris, phosphate and carbonate buffers, and
   optionally, a pH adjusting agent.

14. The aqueous folinate solution according to claim 13, wherein said concentration of sodium folinate is in the range of about 100 to 400 mg of folinic acid per ml.

* * * * *